United States Patent
Carter et al.

(10) Patent No.: US 8,547,062 B2
(45) Date of Patent: *Oct. 1, 2013

(54) APPARATUS AND SYSTEM FOR A BATTERY PACK ASSEMBLY USED DURING MECHANICAL VENTILATION

(75) Inventors: Danis Carter, Valley Center, CA (US); Terry Landis, Solana Beach, CA (US); Thomas Wallner, San Marcos, CA (US); John Leek, San Diego, CA (US)

(73) Assignee: Covidien LP, Mansfield, MA (US)

( * ) Notice: Subject to any disclaimer, the term of this patent is extended or adjusted under 35 U.S.C. 154(b) by 480 days.

This patent is subject to a terminal disclaimer.

(21) Appl. No.: 12/757,124

(22) Filed: Apr. 9, 2010

(65) Prior Publication Data
US 2011/0126829 A1 Jun. 2, 2011

Related U.S. Application Data

(60) Provisional application No. 61/266,008, filed on Dec. 2, 2009, provisional application No. 61/266,012, filed on Dec. 2, 2009.

(51) Int. Cl.
*H01M 10/46* (2006.01)

(52) U.S. Cl.
USPC .......................................... 320/114

(58) Field of Classification Search
USPC ................ 320/107, 112, 114, 115, 116, 132, 320/149
See application file for complete search history.

(56) References Cited

U.S. PATENT DOCUMENTS

| | | |
|---|---|---|
| 3,796,951 A | 3/1974 | Joseph |
| 4,497,881 A | 2/1985 | Bertolino |
| 4,559,456 A | 12/1985 | Yamamoto et al. |
| 4,662,736 A | 5/1987 | Taniguchi et al. |
| 4,752,089 A | 6/1988 | Carter |
| 4,921,642 A | 5/1990 | LaTorraca |
| 4,954,799 A | 9/1990 | Kumar |
| 4,965,462 A | 10/1990 | Crawford |
| 5,015,544 A | 5/1991 | Burroughs et al. |

(Continued)

FOREIGN PATENT DOCUMENTS

| | | |
|---|---|---|
| WO | WO 9617425 | 8/1996 |
| WO | WO 9834314 | 8/1998 |

OTHER PUBLICATIONS

Covidien, "Puritan Bennett 540™ Ventilator," undated, downloaded from Internet website, 2 pages.

(Continued)

*Primary Examiner* — Edward Tso

(57) ABSTRACT

This disclosure describes methods and apparatus for indicating battery cell status on a battery pack assembly used during mechanical ventilation. Embodiments described herein seek to provide methods for indicating battery cell status on the exposed exterior of a battery assembly pack both when the battery is in use and when the battery is not in use during mechanical ventilation. Embodiments utilize power from the ventilator as well as power from the battery pack itself to light the indicators during periods of battery use and non-use, respectively. Embodiments described herein further seek to provide an apparatus indicating battery cell status on the exposed exterior of the battery pack assembly during mechanical ventilation. Embodiments described herein further seek to provide an apparatus for a battery pack assembly used during mechanical ventilation. Embodiments described herein seek to provide a system for a ventilation system with an inserted battery pack assembly.

20 Claims, 7 Drawing Sheets

(56) References Cited

U.S. PATENT DOCUMENTS

| | | |
|---|---|---|
| 5,057,822 A | 10/1991 | Hoffman |
| 5,072,737 A | 12/1991 | Goulding |
| 5,118,962 A | 6/1992 | Ishii et al. |
| 5,149,603 A | 9/1992 | Fleming et al. |
| 5,150,291 A | 9/1992 | Cummings et al. |
| 5,153,496 A | 10/1992 | LaForge |
| 5,156,931 A | 10/1992 | Burroughs et al. |
| 5,159,272 A | 10/1992 | Rao et al. |
| 5,161,525 A | 11/1992 | Kimm et al. |
| 5,216,371 A | 6/1993 | Nagai |
| 5,237,987 A | 8/1993 | Anderson et al. |
| 5,244,754 A | 9/1993 | Bohmer et al. |
| 5,256,500 A | 10/1993 | Ishimoto |
| 5,258,901 A | 11/1993 | Fraidlin |
| 5,271,389 A | 12/1993 | Isaza et al. |
| 5,279,549 A | 1/1994 | Ranford |
| 5,283,137 A | 2/1994 | Ching |
| 5,299,568 A | 4/1994 | Forare et al. |
| 5,301,921 A | 4/1994 | Kumar |
| 5,306,956 A | 4/1994 | Ikeda et al. |
| 5,308,715 A | 5/1994 | Aronne |
| 5,315,228 A | 5/1994 | Hess et al. |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,348,813 A | 9/1994 | Bohmer et al. |
| 5,350,640 A | 9/1994 | Masui |
| 5,351,522 A | 10/1994 | Lura |
| 5,357,946 A | 10/1994 | Kee et al. |
| 5,368,019 A | 11/1994 | LaTorraca |
| 5,369,802 A | 11/1994 | Murray |
| 5,372,898 A | 12/1994 | Atwater et al. |
| 5,383,449 A | 1/1995 | Forare et al. |
| 5,385,142 A | 1/1995 | Brady et al. |
| 5,389,470 A | 2/1995 | Parker et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,418,085 A | 5/1995 | Huhndorff et al. |
| 5,438,980 A | 8/1995 | Phillips |
| 5,443,075 A | 8/1995 | Holscher |
| 5,448,152 A | 9/1995 | Albright |
| 5,449,567 A | 9/1995 | Yeh |
| 5,460,901 A | 10/1995 | Syrjala |
| 5,478,665 A | 12/1995 | Burroughs et al. |
| 5,496,658 A | 3/1996 | Hein et al. |
| 5,513,631 A | 5/1996 | McWilliams |
| 5,514,946 A | 5/1996 | Lin et al. |
| 5,517,983 A | 5/1996 | Deighan et al. |
| 5,520,071 A | 5/1996 | Jones |
| 5,524,615 A | 6/1996 | Power |
| 5,525,439 A | 6/1996 | Huhndorff et al. |
| 5,531,221 A | 7/1996 | Power |
| 5,542,415 A | 8/1996 | Brody |
| 5,544,674 A | 8/1996 | Kelly |
| 5,549,106 A | 8/1996 | Gruenke et al. |
| 5,567,541 A | 10/1996 | Rouhani |
| 5,596,278 A | 1/1997 | Lin |
| 5,596,984 A | 1/1997 | O'Mahoney et al. |
| 5,610,497 A | 3/1997 | Croughwell |
| 5,630,411 A | 5/1997 | Holscher |
| 5,632,270 A | 5/1997 | O'Mahoney et al. |
| 5,635,813 A | 6/1997 | Shiga et al. |
| 5,640,150 A | 6/1997 | Atwater |
| 5,641,587 A | 6/1997 | Mitchell et al. |
| 5,645,048 A | 7/1997 | Brodsky et al. |
| 5,656,919 A | 8/1997 | Proctor et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,677,077 A | 10/1997 | Faulk |
| 5,715,812 A | 2/1998 | Deighan et al. |
| 5,738,954 A | 4/1998 | Latella et al. |
| 5,762,480 A | 6/1998 | Adahan |
| 5,771,884 A | 6/1998 | Yarnall et al. |
| 5,789,100 A | 8/1998 | Burroughs et al. |
| 5,791,339 A | 8/1998 | Winter |
| 5,794,986 A | 8/1998 | Gansel et al. |
| 5,813,399 A | 9/1998 | Isaza et al. |
| 5,825,100 A | 10/1998 | Kim |
| 5,826,575 A | 10/1998 | Lall |
| 5,829,441 A | 11/1998 | Kidd et al. |
| 5,861,812 A | 1/1999 | Mitchell et al. |
| 5,864,938 A | 2/1999 | Gansel et al. |
| 5,865,168 A | 2/1999 | Isaza |
| 5,867,007 A | 2/1999 | Kim |
| 5,881,717 A | 3/1999 | Isaza |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 5,939,799 A | 8/1999 | Weinstein |
| 5,978,236 A | 11/1999 | Faberman et al. |
| 6,024,089 A | 2/2000 | Wallace et al. |
| 6,041,780 A | 3/2000 | Richard et al. |
| 6,045,398 A | 4/2000 | Narita et al. |
| 6,047,860 A | 4/2000 | Sanders |
| 6,054,234 A | 4/2000 | Weiss et al. |
| 6,076,523 A | 6/2000 | Jones et al. |
| 6,084,380 A | 7/2000 | Burton |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony |
| 6,153,947 A | 11/2000 | Rockow et al. |
| 6,156,450 A | 12/2000 | Bailey |
| 6,161,539 A | 12/2000 | Winter |
| 6,184,656 B1 * | 2/2001 | Karunasiri et al. ........... 320/119 |
| 6,220,245 B1 | 4/2001 | Takabayashi et al. |
| 6,232,782 B1 | 5/2001 | Kacprowicz et al. |
| 6,259,171 B1 | 7/2001 | Cheng |
| 6,269,812 B1 | 8/2001 | Wallace et al. |
| 6,273,444 B1 | 8/2001 | Power |
| 6,283,119 B1 | 9/2001 | Bourdon |
| 6,304,005 B1 | 10/2001 | Aoki et al. |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,330,176 B1 | 12/2001 | Thrap et al. |
| 6,357,438 B1 | 3/2002 | Hansen |
| 6,360,745 B1 | 3/2002 | Wallace et al. |
| 6,366,054 B1 | 4/2002 | Hoenig et al. |
| 6,369,838 B1 | 4/2002 | Wallace et al. |
| 6,384,491 B1 | 5/2002 | O'Meara |
| 6,412,483 B1 | 7/2002 | Jones et al. |
| 6,439,229 B1 | 8/2002 | Du et al. |
| 6,467,478 B1 | 10/2002 | Merrick et al. |
| 6,509,657 B1 | 1/2003 | Wong et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,603,273 B1 | 8/2003 | Wickham et al. |
| 6,621,250 B1 | 9/2003 | Ohkubo et al. |
| 6,622,726 B1 | 9/2003 | Du |
| 6,639,385 B2 | 10/2003 | Verbrugge et al. |
| 6,644,310 B1 | 11/2003 | Delache et al. |
| 6,668,824 B1 | 12/2003 | Isaza et al. |
| 6,675,801 B2 | 1/2004 | Wallace et al. |
| 6,718,974 B1 | 4/2004 | Moberg |
| 6,725,447 B1 | 4/2004 | Gilman et al. |

| | | |
|---|---|---|
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,814,074 B1 | 11/2004 | Nadjafizadeh et al. |
| 6,866,040 B1 | 3/2005 | Bourdon |
| 6,891,352 B2 | 5/2005 | Miyazaki et al. |
| 6,899,103 B1 | 5/2005 | Hood et al. |
| 6,924,567 B2 | 8/2005 | Killian et al. |
| 6,952,084 B2 | 10/2005 | Bruwer |
| 6,960,854 B2 | 11/2005 | Nadjafizadeh et al. |
| 6,979,502 B1 | 12/2005 | Gartstein et al. |
| 7,005,835 B2 | 2/2006 | Brooks et al. |
| 7,009,401 B2 | 3/2006 | Kinoshita et al. |
| 7,036,504 B2 | 5/2006 | Wallace et al. |
| 7,077,131 B2 | 7/2006 | Hansen |
| 7,080,646 B2 | 7/2006 | Wiesmann et al. |
| RE39,225 E | 8/2006 | Isaza et al. |
| 7,117,438 B2 | 10/2006 | Wallace et al. |
| RE39,703 E | 6/2007 | Burroughs et al. |
| 7,248,020 B2 | 7/2007 | Hidaka et al. |
| 7,252,088 B1 | 8/2007 | Nieves Ramírez |
| 7,268,660 B2 | 9/2007 | Bolda et al. |
| 7,270,126 B2 | 9/2007 | Wallace et al. |
| 7,320,321 B2 | 1/2008 | Pranger et al. |
| 7,339,350 B2 | 3/2008 | Kubale et al. |
| 7,369,757 B2 | 5/2008 | Farbarik |
| 7,370,650 B2 | 5/2008 | Nadjafizadeh et al. |
| 7,400,113 B2 | 7/2008 | Osborne |
| RE40,506 E | 9/2008 | Burroughs et al. |
| 7,428,902 B2 | 9/2008 | Du et al. |
| 7,460,959 B2 | 12/2008 | Jafari |
| 7,482,941 B2 | 1/2009 | Bruce et al. |
| 7,487,773 B2 | 2/2009 | Li |
| 7,654,802 B2 | 2/2010 | Crawford, Jr. et al. |
| 7,694,677 B2 | 4/2010 | Tang |
| 7,717,113 B2 | 5/2010 | Andrieux |
| 7,721,736 B2 | 5/2010 | Urias et al. |
| D618,356 S | 6/2010 | Ross |
| 7,741,815 B2 | 6/2010 | Cassidy |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| D649,157 S | 11/2011 | Skidmore et al. |
| 8,113,062 B2 | 2/2012 | Graboi et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0011845 A1 | 8/2001 | Simonelli et al. |
| 2005/0039748 A1 | 2/2005 | Andrieux |
| 2005/0052085 A1 | 3/2005 | Chang et al. |
| 2005/0139212 A1 | 6/2005 | Bourdon |
| 2006/0144396 A1* | 7/2006 | DeVries et al. .......... 128/204.21 |
| 2007/0017515 A1 | 1/2007 | Wallace et al. |
| 2007/0068518 A1 | 3/2007 | Urias et al. ............... 128/200.24 |
| 2007/0077200 A1 | 4/2007 | Baker |
| 2007/0105010 A1 | 5/2007 | Cassidy .......................... 429/90 |
| 2007/0152630 A1 | 7/2007 | Winkler et al. |
| 2007/0227537 A1 | 10/2007 | Bemister et al. |
| 2007/0273216 A1 | 11/2007 | Farbarik |
| 2007/0284361 A1 | 12/2007 | Nadjafizadeh et al. |
| 2008/0053441 A1 | 3/2008 | Gottlib et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0104929 A1 | 4/2010 | Schäfer et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0253288 A1 | 10/2010 | Cassidy |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0126829 A1* | 6/2011 | Carter et al. ............ 128/202.22 |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0175728 A1 | 7/2011 | Baker, Jr. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0221384 A1* | 9/2011 | Scheucher .................... 320/101 |
| 2011/0259330 A1 | 10/2011 | Jafari et al. |

OTHER PUBLICATIONS

Covidien, "Puritan Bennett 540™ Ventilator," undated, downloaded from internet website, 6 pages.

U.S. Appl. No. 12/757,131, Notice of Allowance mailed Dec. 17, 2012, 8 pgs.

U.S. Appl. No. 12/757,131, Notice of Allowance mailed Sep. 4, 2012, 9 pgs.

7200 Series Ventilator, Options, and Accessories: Operators Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

\* cited by examiner

APPARATUS AND SYSTEM FOR A BATTERY PACK ASSEMBLY USED DURING MECHANICAL VENTILATION

RELATED APPLICATIONS

This application claims the benefit of U.S. Provisional Application No. 61/266,012, filed Dec. 2, 2009, which application is hereby incorporated by reference. This application claims the benefit of U.S. Provision Application No. 61/266,008, filed Dec. 2, 2009, which application is hereby incorporated by reference.

INTRODUCTION

A ventilator is a device that mechanically helps patients breathe by replacing some or all of the muscular effort required to inflate and deflate the lungs. Some ventilators are designed as transportable instruments that can provide ventilation to a patient while the patient is being transported between locations. As a transportable instrument, a ventilator needs constant power to provide ventilatory assistance both when the ventilator is stationary and when the ventilator is mobile. Ventilators typically achieve a constant power supply by employing an external power source or outlet when the ventilator is stationary and battery power when the ventilator is mobile.

One problem with powering a transportable ventilator is monitoring the charge on batteries used as a power source when the ventilator is mobile. Some batteries used in ventilators attempt to alleviate this concern by providing indicators on the outside of the battery. These indicators display the remaining charge in a given battery. The indicators, however, are typically located on a side of the battery that is not visible to the user when the battery is inserted into the ventilator. In other words, the user needs to remove the battery from the ventilator to view its remaining charge. Removing a battery pack when the ventilator is relying on battery power can risk the operation of the ventilator as well as the ultimate health of the ventilatory patient.

Apparatus and System for a Battery Pack Assembly Used During Mechanical Ventilation This disclosure relates to an apparatus, method, and system for indicating battery cell status on a battery pack assembly used during mechanical ventilation. The battery cell status is displayed on the exposed exterior of the battery pack assembly so that a user can view battery cell status without removing the battery from the ventilator.

Embodiments described herein seek to provide methods for indicating battery cell status on the exposed exterior of a battery assembly pack both when the battery is in use and when the battery is not in use during mechanical ventilation. Embodiments utilize power from the ventilator as well as power from the battery pack itself to light the indicators during periods when the battery pack assembly is supplying power to the host and when the battery pack assembly is receiving power from a host.

Embodiments described herein seek to provide an apparatus indicating battery cell status on the exposed exterior of the battery pack assembly during mechanical ventilation.

Embodiments described herein seek to provide an apparatus for a battery pack assembly used during mechanical ventilation.

Embodiments described herein seek to provide a system for a ventilation system with an inserted battery pack assembly.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of devices, the present disclosure will discuss the implementation of these techniques for use in a mechanical ventilator system. The reader will understand that the battery pack assembly could be implemented in other technologies providing power by both one or more battery pack assemblies and a separate power supply.

The disclosure describes methods and apparatus for indicating battery cell status on the exterior of a battery pack assembly. The disclosure further describes a battery pack assembly used during mechanical ventilation. The disclosure discusses scenarios when the battery pack assembly is "in use" and when the battery pack assembly is "not in use." Describing a battery pack assembly as "in use" means that the battery pack assembly inserted into a host is the source of power for the host, such as a ventilator. Describing a battery pack assembly as "not in use" means that a battery pack assembly inserted into a host is not the source of power for the host. When the battery pack assembly is "not in use", the host is receiving power from another source (i.e. external power source or plug) or is off. During times when the battery pack assembly is "not in use" but the ventilator is receiving power from another source the battery pack assembly may or may not be being charged by the power supplied by the ventilator's power source.

Figure 1:
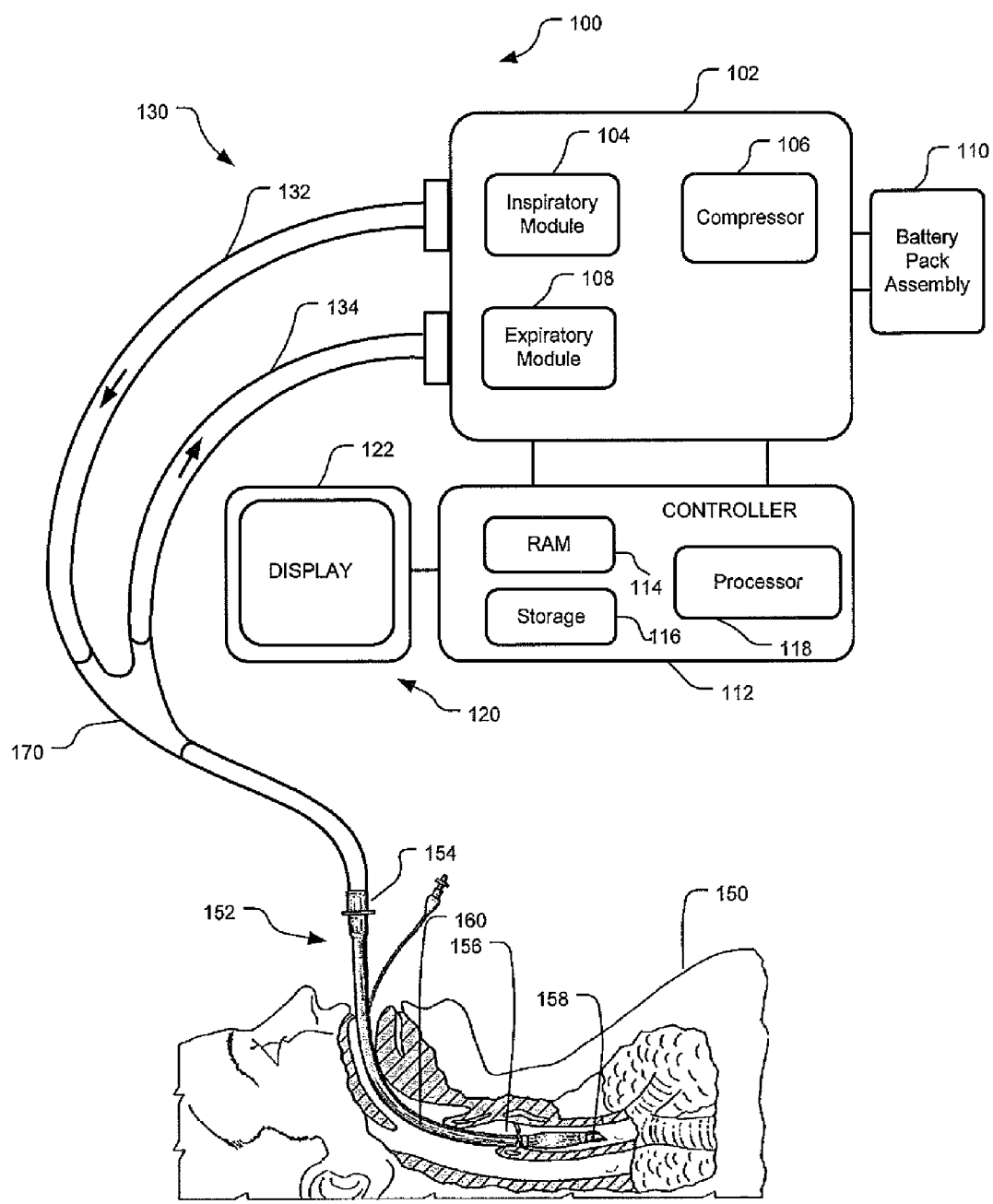
FIG. 1 is a diagram illustrating a representative ventilator system utilizing an endotracheal tube for air delivery to a patient's lungs.

FIG. 1 illustrates an embodiment of a ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive patient interface 152.

Ventilation may be achieved by invasive or non-invasive means. Invasive ventilation, such as invasive patient interface 152, utilizes a breathing tube, particularly an endotracheal tube (ET tube) or a tracheostomy tube (trach tube), inserted into the patient's trachea in order to deliver air to the lungs. Non-invasive ventilation may utilize a mask or other device placed over the patient's nose and mouth. For the purposes of this disclosure, an invasive patient interface 152 is shown and described, although the reader will understand that the technology described herein is equally applicable to any invasive or non-invasive patient interface.

Airflow is provided via ventilation tubing circuit 130 and invasive patient interface 152. Ventilation tubing circuit 130 may be a dual-limb (shown) or a single-limb circuit for carrying gas to and from the patient 150. In a dual-limb embodiment as shown, a "wye fitting" 170 may be provided to couple the patient interface 154 to an inspiratory limb 132 and an expiratory limb 134 of the ventilation tubing circuit 130.

Pneumatic system 102 may be configured in a variety of ways. In the present example, system 102 includes an expiratory module 110 coupled with the expiratory limb 134 and an inspiratory module 104 coupled with the inspiratory limb 132. Compressor 106 or another source(s) of pressurized gases (e.g., air, oxygen, and/or helium) is coupled with inspiratory module 104 to provide a gas source for ventilatory support via inspiratory limb 132.

One or more battery pack assemblies 110 may also be inserted into the ventilator at one or more locations. A battery pack assembly 110 inserted into the backplane of the compressor 106, so that the battery pack assembly 110 is communicatively connected with the compressor 106, can be used as an internal source of power for the ventilator. A battery pack assembly 110 inserted into the side of the ventilator can be used as a back-up battery pack assembly 110. In one embodiment, one or more battery pack assemblies 110 are inserted into the backplane of the compressor 106 and one or more battery pack assemblies are inserted into the side of the ventilator.

The pneumatic system may include a variety of other components, including sources for pressurized air and/or oxygen, mixing modules, valves, sensors, tubing, accumulators, filters, etc. Controller 112 is operatively coupled with pneumatic system 102, signal measurement and acquisition systems, and an operator interface 120 may be provided to enable an operator to interact with the ventilator 100 (e.g., change ventilator settings, select operational modes, view monitored parameters, etc.). Controller 112 may include memory 114, one or more processors 118, storage 116, and/or other components of the type commonly found in command and control computing devices.

The memory 114 is computer-readable storage media that stores software that is executed by the processor 118 and which controls the operation of the ventilator 100. In an embodiment, the memory 114 includes one or more solid-state storage devices such as flash memory chips. In an alternative embodiment, the memory 114 may be mass storage connected to the processor 118 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 118. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The controller 112 issues commands to pneumatic system 102 in order to control the breathing assistance provided to the patient by the ventilator. The specific commands may be based on inputs received from patient 150, pneumatic system 102 and sensors, operator interface 120 and/or other components of the ventilator. In the depicted example, operator interface includes a display 122 that is touch-sensitive, enabling the display to serve both as an input and output device. The display 122 is configured to display information received from the battery pack assembly 110.

The controller 112 may also control the operation of battery pack assembly 110 provided with the pneumatic system 102. For example, in an embodiment the controller 112 may control the charging of the battery pack assemblies when they are not in use. Such control may include sensing the current charge state or states associated with the battery packs and charging them as needed based on the charge state and type of battery technology used (e.g., trickle charging or periodic charging as appropriate for the battery chemistry). Control may also include managing the transition between using power from the battery pack assemblies and other sources of power so that the ventilation of the patient is not interrupted or adversely affected.

In yet another embodiment, control may include monitoring and issuing alarms related to battery cell status. This may include issuing alarms or status notifications through the system's display 122 in addition to any information provided via the battery pack assemblies themselves. Such monitoring may also include communication between the battery pack assemblies and the controller 112. For example, the controller 112 may provide power and/or commands to the battery pack assembly 110 in addition to receiving information from the battery pack assemblies.

In yet another embodiment, control of ventilatory functions can be allocated between multiple controllers. For example, one controller could operate breathing assistance (not shown). Another controller could operate ventilatory battery charging and selection (not shown). Another controller could operate compressor charging and selection (not shown). Another controller could operate the displays (not shown).

Figure 2A:
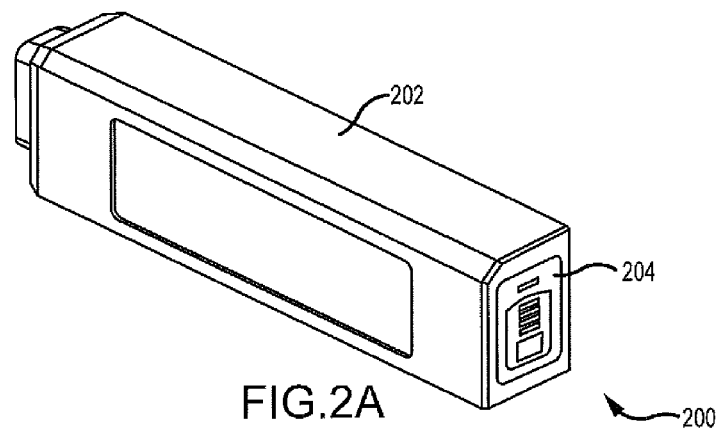
FIG. 2A is an illustration of the exterior of a battery pack assembly that can be used during mechanical ventilation from the LED end.
Figure 2B:
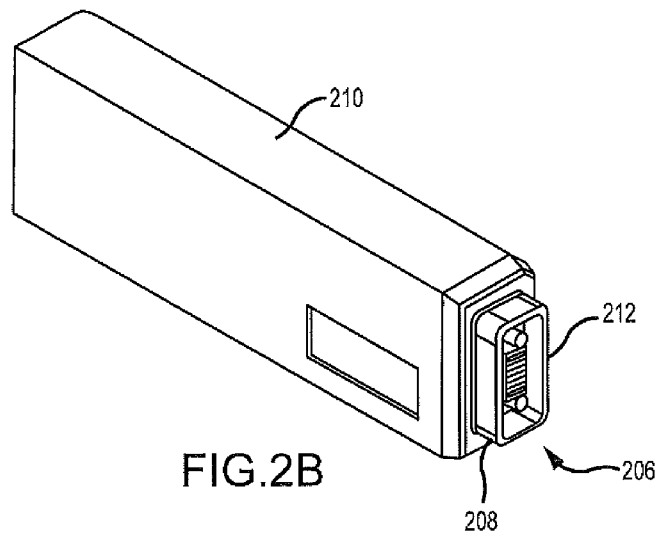
FIG. 2B is an illustration of the exterior of a battery pack assembly that can be used during mechanical ventilation from the connector end.

FIG. 2A-2B provide views of the battery pack assembly from the Battery Pack Status Indicator Panel end and from the connector end, respectively.

FIG. 2A illustrates a view of a battery pack assembly from the Battery Pack Assembly Status Indicator Panel end. The battery pack assembly is enclosed by a battery enclosure 202. The battery enclosure 202 surrounds the battery pack assembly and protects the internal circuitry. At one end of the battery pack assembly is the Battery Pack Assembly Status Indicator Panel 204. As discussed herein, the Battery Pack Assembly Status Indicator Panel 204 is visible to the user without requiring the user to remove the inserted battery pack assembly to view the information displayed on the Battery Pack Assembly Status Indicator Panel 204.

FIG. 2B illustrates a view of a battery pack assembly from the connector end. The battery pack assembly is enclosed by a battery enclosure 210. The battery enclosure 210 surrounds the battery pack assembly and protects internal circuitry. At the other end of the battery pack assembly is the connector 208. The connector 208 is situated within a notch 212 of the of the battery enclosure 210. The notch 212 is designed to fit into a mating connector at the ventilator or at the compressor. As discussed herein, the connector 208 is communicatively coupled with the mating connector at the ventilator or at compressor 106. The connector 208 is slid into the mating connector on the compressor 106 when the battery pack is installed as the internal battery. The connector 208 is slid into the mating connector on the side of the ventilator when installed as an external backup battery.

Figure 3:
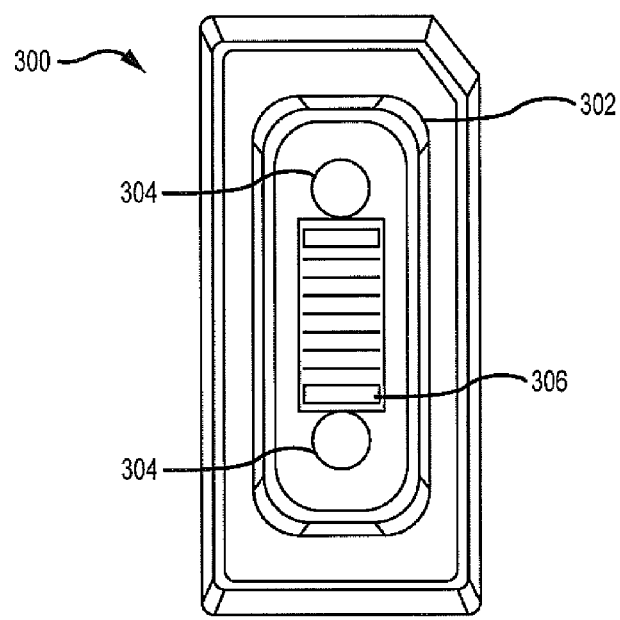
FIG. 3 is an illustration of a connector of a battery pack assembly that can be used during mechanical ventilation.

FIG. 3 provides a more detailed view of the connector 208. The connector 300 is surrounded by a protective shroud 302. The shroud 302 protects the pins 304 and blades 306 of the connector 208. The blades 306 provide a mating cavity for a mating connector at the ventilator or at the compressor. The pins 304 receive analog input and provide for serial communication, temperature monitoring, external lamp control, and Vcc standby current between the connector 208 and the mating connector at the ventilator or at the compressor. The pins 304 include + and − power pins. The + and − power pins are capable of accepting charge provided by a mating connector or driving a load.

Figure 4:
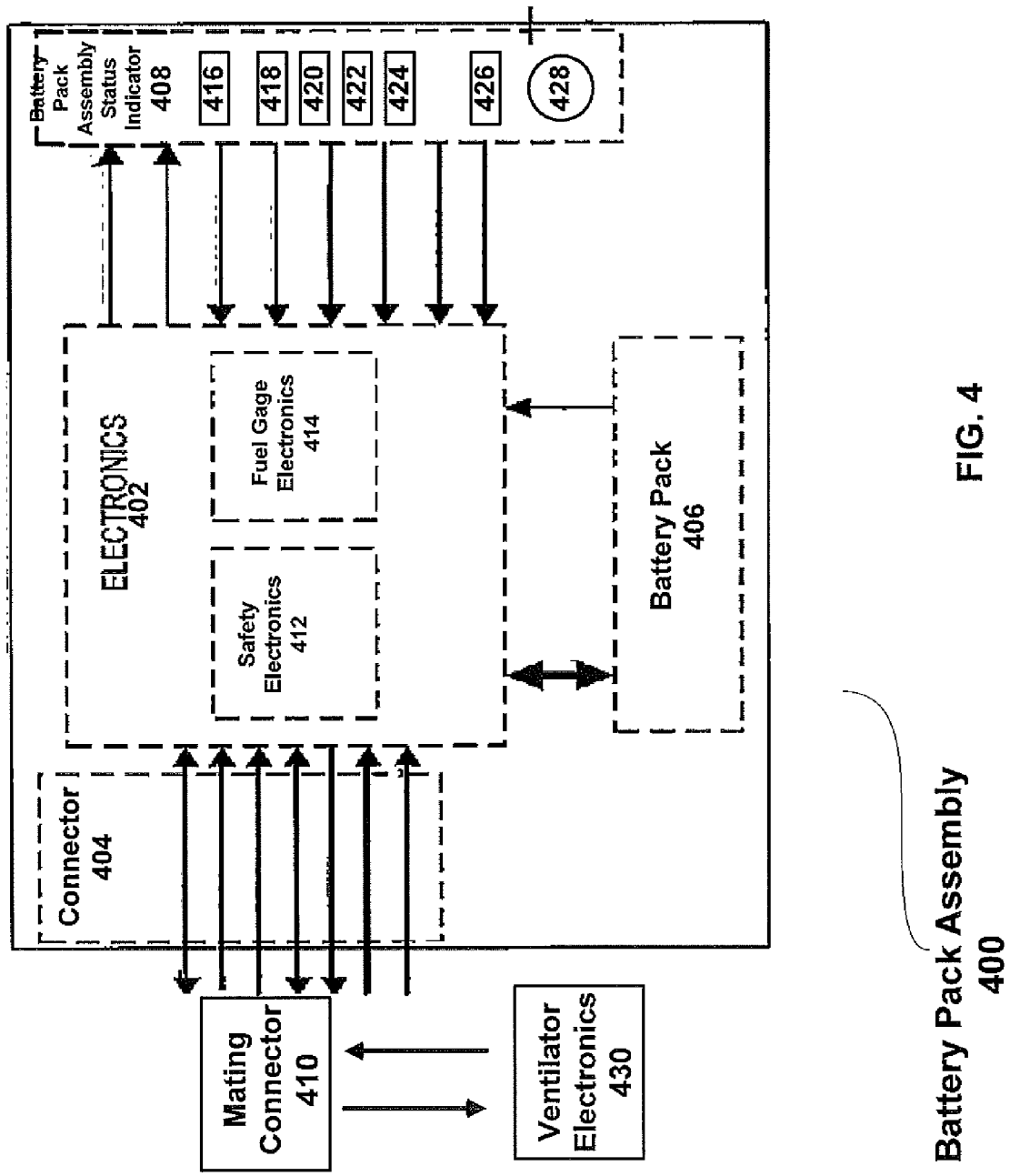
FIG. 4 is an illustration of a battery pack assembly that can be used during mechanical ventilation.

FIG. 4 illustrates another embodiment of a battery pack assembly 400. The battery pack assembly 400 includes a battery pack 406. In one embodiment, the battery pack 406 contains battery cells that are wired to produce a nominal cell voltage that may deviate based on the state-of-charge and temperature of the battery cells. The battery cells in the battery pack 406 can be composed of any suitable material/battery chemistry including but not limited to lithium ion manganese.

The battery pack assembly 400 also includes a connector 404 such as the connector 300 described in FIG. 3. The connector 404 is communicatively coupled to the mating connector 410 at the ventilator or at the compressor. As discussed above, the connector 404 contains return and signal pins for communication with the mating connector 410. The connector 404 communicates battery cell status information to electronics 430 of the ventilator through a mating connector 410 at the ventilator or at the compressor. In one embodiment, electronics 430 of the ventilator include a two wire system management bus. The electronics 430 of the ventilator is further configured to interrogate the fuel gauge electronics 414 about the battery cell status information through the connector 404. Battery cell status information can include state-of charge, battery current, voltage, assembly number, revision, number of discharges, and number of charges. The connector 404 contains individual pins 304 each of which correspond to each indicator 416, 418, 420, 422, 424, and 426 contained in the Battery Pack Assembly Status Indicator Panel 408. The individual pins 304 allows the ventilator to control and/or directly power the indicators 416, 418, 420, 422, 424, and 426 when the battery pack assembly 400 is inserted into the ventilator and is not use.

In one embodiment, the battery pack assembly 400 is "hot-swappable" meaning that a battery pack assembly may be removed or inserted at any time without adversely affecting the operation of the ventilator. In one embodiment of a "hot-swappable" battery pack assembly, the pins in the mating connector 410 are different lengths so that some pins are short pins. When the battery pack assembly 400 is removed, the mating connector 410 disconnects from the connector 404 first at the connections between the short pins of the mating connector 430 and the pins of the connector 404. Disconnecting the short pins of the mating connector 430 from the connector 404 sends a signal to the ventilator controller indicating impending pack removal. The controller can react by disconnecting power from the exiting battery and reconnecting or to another battery. Disconnecting power on other pins of the battery connector is important to protect from arcing currents, potentially damaging to the contacts. This signal may also be used to disable other pins of the connector to protect against any electrical interference that could be caused during the making/breaking of contact between the pins of the connectors. A similar signal may be generated when detecting the insertion of a battery pack assembly into the ventilator.

The battery pack assembly 400 also includes electronics 402. The electronics 402 are controlled by circuits. In one embodiment, the circuits are fuel gage and safety integrated circuit devices manufactured by Texas Instruments. The electronics 402 further include safety electronics 412 and fuel gauge electronics 414.

The fuel gauge electronics 414 are configured to monitor the state of charge of the battery pack 406. The fuel gauge electronics 414 receive information about battery charge from the battery pack 406. When the battery pack assembly 400 is not in use by the ventilator, the fuel gauge electronics determine which of the charge indicators 418, 420, 422, and 424 are lit in response to a depressed test switch 428.

The fuel gauge electronics 414 also protect the battery pack 406 against over-discharge. The fuel gage electronics 414 send the battery pack cell status to the electronics 430 of the ventilator through the connector 404. If the electronics 430 of the ventilator detects a low voltage, the electronics 430 of the ventilator disconnects the ventilator from the battery pack assembly 400 and connects to a different battery pack assembly. If the battery pack 406 were somehow discharged further, the battery pack assembly 400 will disconnect.

The fuel gage electronics 414 also monitor the charge of the battery pack 406 so that, if the charge exceeds an unsafe level the battery pack 406 will disconnect from any charging source. In one embodiment, the battery pack 406 is charged to an amount of about 100 Watts/hrs. Furthermore, the battery pack 406 may have a back up detection of failure and a fuse may be permanently opened if the charge goes beyond the amount.

The fuel gage electronics 414 are further configured to alert a user when the battery pack assembly 400 has undergone fault. Fault can occur as a result of change in battery temperature, voltage, discharge, charge, or current. By means of example and not limitation, a thermistor can be used to detect increased temperature in the battery pack assembly 400 and can communicate an increased temperature fault to the fuel gage electronics 414. The fuel gage electronics 414 then communicate the fault to the electronics 430 of the ventilator through the connector 404 and the mating connector 404. The electronics of the ventilator 430 provide charge to light a fault indicator 426 on the LED fuel gauge 408 on the battery pack assembly 400.

The safety electronics 412 protect the internal circuitry and cells of the Battery Pack 406. The safety electronics 412 are wired with protection circuitry to prevent over-charge and over-discharge of the battery pack 406.

The battery pack assembly 400 further includes a Battery Pack Assembly Status Indicator Panel 408. The Battery Pack Assembly Status Indicator panel 408 includes indicators 416, 418, 420, 422, 424, and 426 and test switch 428. The indicators 416, 418, 420, 422, 424, and 426 and test switch 428 are located on the exposed exterior of the battery pack assembly 400 so that the indicators 416, 418, 420, 422, 424, and 426 and test switch 428 are visible to a user without requiring the user to disconnect the battery pack assembly 400 from the host. In one embodiment, the capacity indicators 418, 420, 422, 424 display approximate charge of the battery pack 406 and the fact that the battery pack 406 is being charged. While four rectangular indicators are illustrated in this example, any number of capacity indicators of any shape can be used. The capacity indicators 418, 420, 422, 424 continuously display available charge of the battery pack 406 in green when the battery pack assembly 400 is in use by the ventilator. While the color green is used in this example any color may be used to display battery charge. Furthermore, if a different type of display is used, such as an alpha-numeric display, the display may be, for example, numeric to correspond with the type of display. When the battery pack assembly 400 is not in use by the ventilator, the available charge may be displayed in response to a user depressing a test switch 428.

In an embodiment, each of the capacity indicators 418, 420, 422, 424 represents a percentage of full capacity of battery charge. The percentage may be based on the absolute capacity or based on an effective or usable capacity range noting that in some battery chemistries it is desirable to maintain the battery within a range (e.g., between 30% and 95% of absolute charge). In one embodiment, each of the capacity indicators 418, 420, 422, 424 represents a quarter of the full (or effective) capacity of battery charge, although any percentage of charge can be used. The bottom capacity indicator 424 does not light until battery charge has reached 25%, the second capacity indicator 422 does not light until the battery charge has reached 50%, and the third capacity indicator 420 does not light until the battery charge has reached 75%. The top capacity indicator 418 represents 100% charge and so it does not light until charging is complete and the battery has reported end of charge state. While the present embodiment contemplates lighting the capacity indicators 418, 420, 422, 424 from bottom to top during charge, any sequence of lighting the capacity indicators is contemplated in the scope of the invention.

A battery pack can be charged by either a ventilator when inserted into the ventilator or an external charger when not inserted into the ventilator. The following example discusses charge by a ventilator when the battery pack is inserted into the ventilator. Similar mechanisms can be utilized by an external charger charging a stand alone battery pack assembly. In an embodiment, certain indicators may be used to indicate when a battery pack assembly is charging. For example, during charge, the two capacity indicators that would indicate a cumulative 50% charge level are constantly lit. In one embodiment, the two capacity indicators that indicate a cumulative 50% charge are the two bottom capacity indicators 424 and 422. The remaining capacity indicators 418 and 420 are under control of the ventilator during charge and flash to indicate charging activity. For example, charging from 60% charge upwards would have the bottom two capacity indicators 424 and 422 constantly lit and the two above capacity indicators 418 and 420 would flash in sequence from 420 to 418. As discussed above, if the capacity indicators are instead configured to light from top to bottom, this sequence would be reversed so that the top two capacity indicators 418 and 420 would be constantly lit during charge and the bottom two capacity indicators 422 and 424 would flash in sequence from 422 to 424.

The Battery Pack Assembly Status Indicator Panel 408 also includes an in-use indicator 416. The in-use indicator 416 is lit when the battery pack assembly 400 is in use by the ventilator. When the battery pack assembly 400 is in use, the electronics of the battery pack assembly 400 provide current 404 to light the in-use indicator 416. For example, the in-use indicator 416 may be lit to white when the battery pack assembly 400 is in use. However, any lighting color contemplated may be used. Furthermore, the in-use indicator 416 can be any shape or size.

The Battery Pack Assembly Status Indicator Panel 408 also includes a fault indicator 426. As discussed above, the fault indicator 426 is lit when the battery pack assembly 400 undergoes fault. Fault can occur when an out-of-bounds condition results, for example, and is not limited to the following parameters: change in battery temperature, voltage, discharge, charge, or current. When a fault occurs, the safety electronics 412 communicate the fault to the electronics 430 of the ventilator through the connector 404 and the mating connector 404. The electronics of the ventilator 430 provide the power necessary to light a fault indicator 426 on the Battery Pack Status Indicator Panel 408. The fault indicator 426 can be lit to any color and can be of any shape or size.

The Battery Pack Status Indicator Panel 408 also includes a test switch 428. The test switch 428 allows a user to view the remaining charge of a battery pack assembly 400 when the battery pack assembly 400 is not inserted into the ventilator 400. In other words, the test switch 428 allows a user to view the remaining charge of a stand alone battery pack assembly. When the test switch 428 is depressed, the electronics 402 of the battery pack assembly 400 momentarily activate the indicators 418, 420, 422, 424, and 426 to display the battery cell status information.

Figure 5:
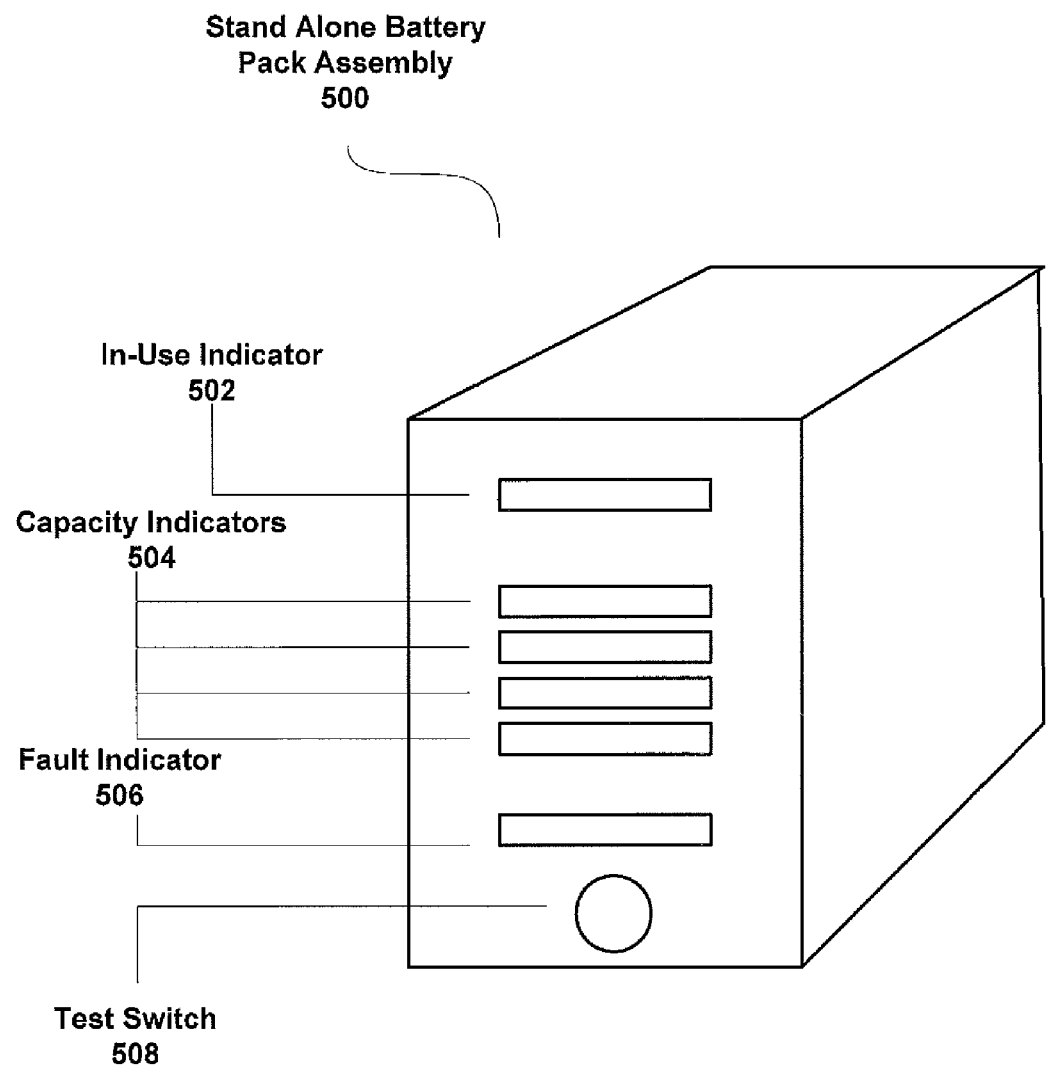
FIG. 5 is an illustration of a stand alone battery pack assembly that can be used during mechanical ventilation.

FIG. 5 illustrates an embodiment of a stand alone battery pack assembly 500. A stand alone battery pack assembly 500 is a battery pack assembly that is not inserted into a host, such as a ventilator. The stand alone battery pack assembly 500 can be charged by inserting the battery pack assembly 500 into a host or by inserting the battery pack assembly 500 into an external charger.

The stand alone battery pack assembly 500 depicts an in-use indicator 502 such as the in-use indicator described in FIG. 4. As discussed above, the in-use indicator is lit when the stand alone battery pack assembly 500 is inserted in and being used as a power source by a host (i.e. ventilator).

The stand alone battery pack assembly 500 also includes capacity indicators 504. The capacity indicators 504 display the battery charge as described in FIG. 4. The capacity indicators 504 are located on the exterior of the stand alone battery pack assembly 500. Displaying the capacity indicators on the exterior of the stand alone battery pack assembly 500 allows the indicators to remain visible to a user if the stand alone battery pack assembly 500 is installed into a host without requiring the user to remove the battery pack assembly 500 from the host. The capacity indicators can utilize any display technology such as LED bar indicators, alpha-numeric display, or any other display technology. Furthermore, the stand alone battery pack assembly 500 can include any number of capacity indicators 504 and the capacity indicators 504 can be any shape or size.

The stand alone battery pack assembly 500 also includes a fault indicator 506. The fault indicator 506 is lit when the battery has undergone fault as discussed with regard to FIG. 4.

The stand alone battery pack assembly 500 also includes a test switch 508. The test switch 508 allows a user to test the capacity of the battery pack assembly 500 when the battery pack assembly 500 is not in use by the ventilator. The test switch 528 can be any type of switch including but not limited to a mechanical snap-action switch or a membrane switch. When the user depresses the test switch 528, the capacity indicators 504 are momentarily lit as described with regard to FIG. 4.

Figure 6:
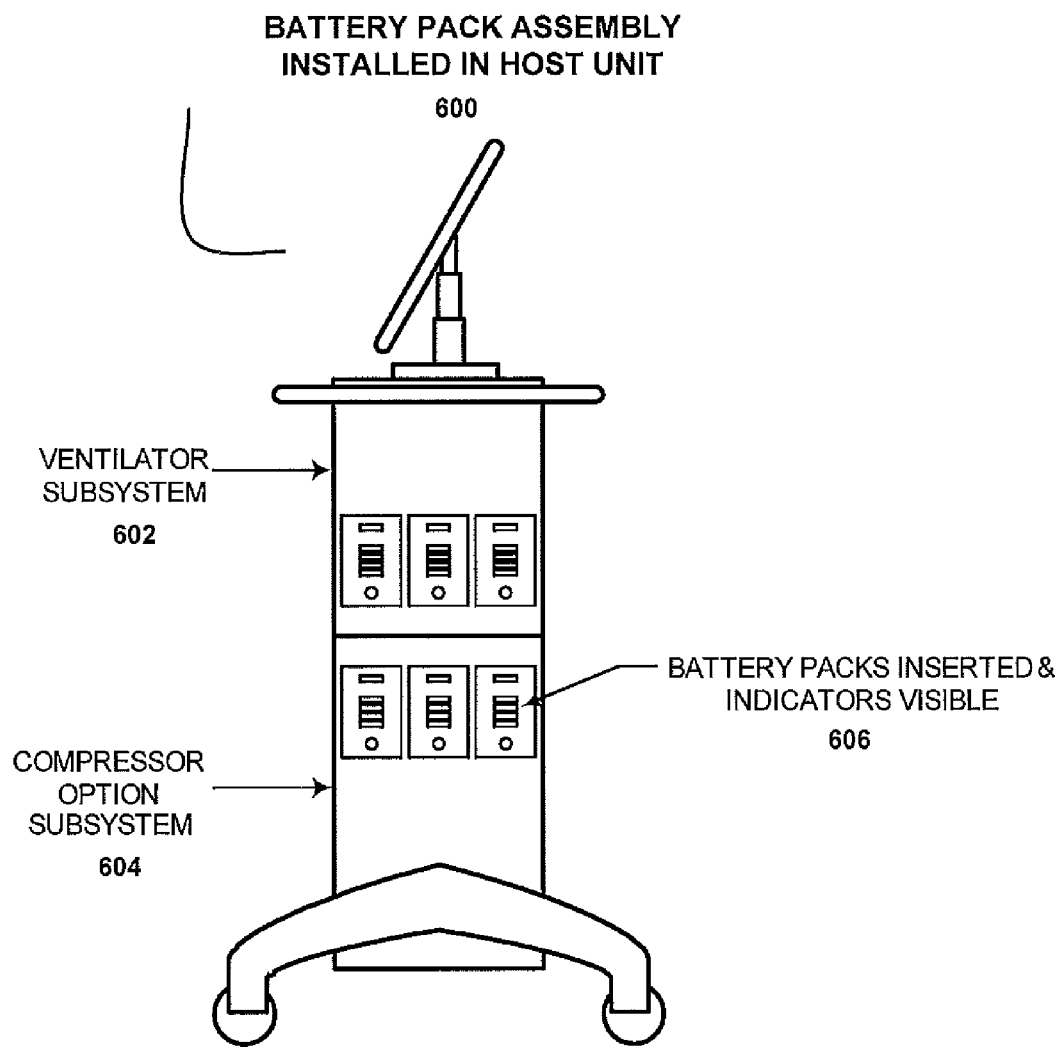
FIG. 6 is an illustration of a battery pack assembly that can be used during mechanical ventilation inserted in a host unit.

FIG. 6 depicts a battery pack assembly 500 installed in a host unit 600. In one embodiment, the host unit is a ventilator.

The ventilator is a transportable instrument 600 and, as a transportable unit, relies on power provided by one or more battery pack assemblies 606 inserted into the host unit when the host unit is not connected to wall power. In one embodiment, the battery pack assemblies 606 are inserted into both the ventilator subsystem 602 and the compressor option subsystem 604. The one or more battery pack assemblies 606 inserted into the ventilator subsystem 602 are inserted so that the connector 404 of the battery pack assembly 400 connects with a mating connector 410 at the ventilator. The one or more battery pack assemblies 606 inserted into the compressor option subsystem 604 are inserted so that the connecter 404 of the battery pack assembly 400 connects with a mating connector 410 communicatively coupled to the compressor 106.

The one or more inserted battery pack assemblies 606 include an in-use indicator 502, capacity indicators 504, a fault indicator 506, and a test switch 508 that are visible to a user of the ventilator without requiring the user the remove the battery pack assembly 500 to view the display. Multiple battery pack assemblies 606 allow a user to view the battery cell status information of different battery pack assemblies and, consequentially, have more options in powering the ventilator. In one embodiment, three battery pack assemblies 606 are inserted into the ventilator subsystem as back-up battery pack assemblies and three battery pack assemblies 606 are inserted into the compressor option subsystem 604 as the internal power source.

Figure 7:
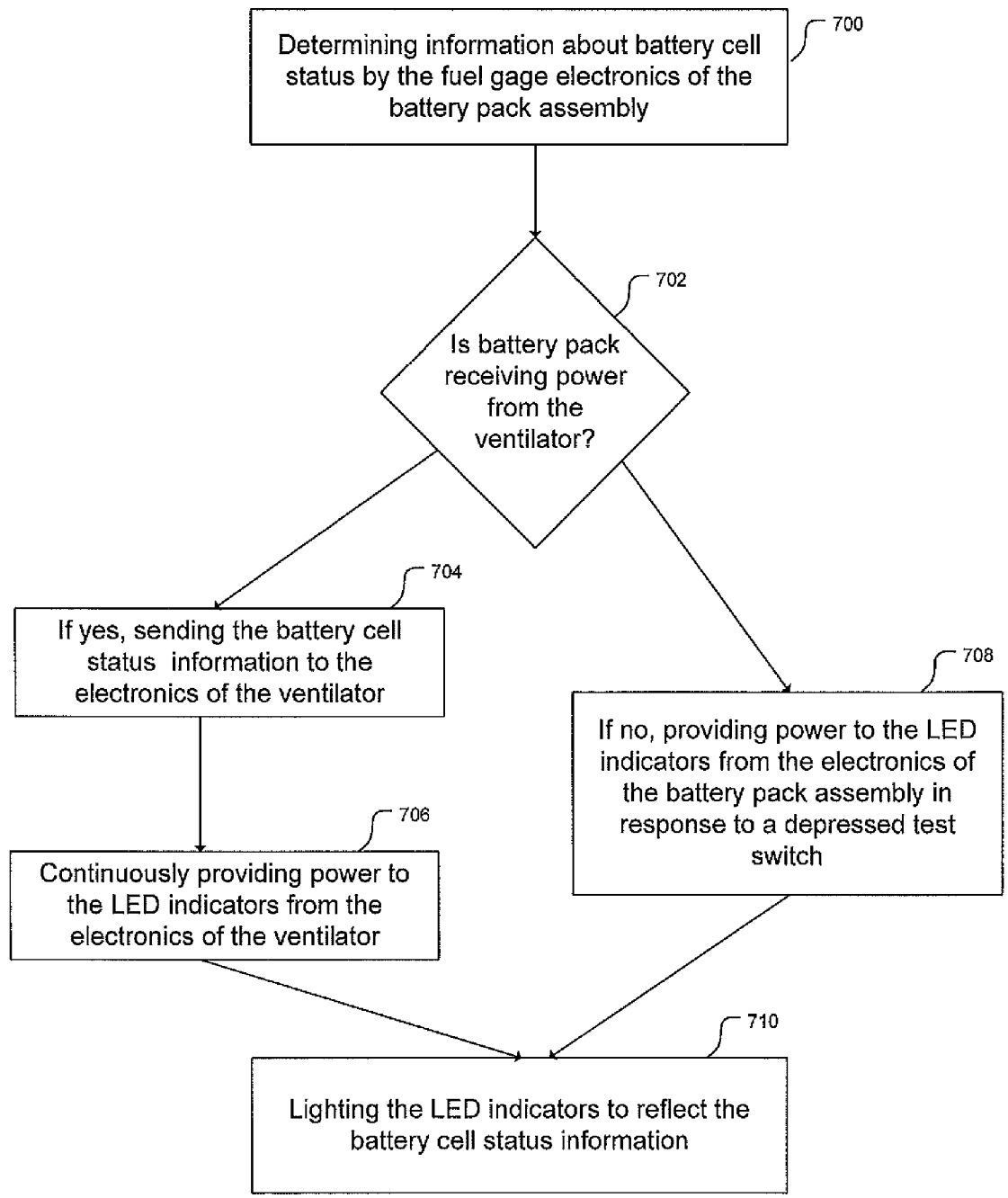
FIG. 7 is a flow chart of a method for indicating battery cell status on a battery pack assembly used during mechanical ventilation.

FIG. 7 illustrates a flow chart of a method for indicating battery cell status. At step 700 information about battery cell status is determined by the fuel-gage received from the battery pack at the electronics of the battery pack. As discussed above, information about battery cell status can include state of charge, battery current, voltage, assembly number, revision, number of discharges, number of charges, date, in-use status, and fault.

At step 702 a determination is made whether the battery pack assembly is receiving power from a host, such as a ventilator. A battery pack assembly is receiving power from a ventilator when the battery pack assembly is inserted into the ventilator and the ventilator is connected to wall both turned on and receiving power from an external power source. A battery pack assembly is not receiving power from a ventilator when the battery pack assembly is in use providing power to the ventilator. A battery pack assembly is also not receiving power from a ventilator when the battery pack assembly is not inserted into the ventilator. This can occur when the battery pack assembly is a stand alone battery pack assembly 500 or when the battery pack assembly is being charged by an external charger.

At step 704 the battery cell status information is sent to the electronics, e.g., the controller, of the ventilator if the battery pack assembly is receiving power from the ventilator. As discussed above, the battery cell status information is sent to the electronics of the ventilator through a connector communicatively coupled to a mating connector at the ventilator or at the compressor.

At step 706 the electronics of the ventilator provide continuous power to the LED indicators. This continuous charge allows the LED indicators to remain lit while the battery pack assembly is receiving power from the ventilator.

At step 708 the method proceeds from step 700 in a situation where the battery pack assembly is not receiving power from the ventilator. At step 708 the electronics of the battery pack assembly provide power to the LED indicators so that they display the current charge state of the battery pack assemblies. In one embodiment, the charge is provided in response to a depressed test switch when the battery pack assembly is a stand alone battery pack assembly. When the test switch is depressed, the electronics of the battery pack assembly provide a momentary charge that light up the LED indicators. The momentary charge allows a user to view the battery cell status information displayed by the indicators without significantly draining the battery by requiring continuous charge. In another embodiment, the battery pack assembly is in use and the charge is provided on a continual basis.

At step 710, the method concludes when the LED indicators are lit to reflect the battery cell status information. Specifically, the in-use indicator will be lit when the battery pack assembly is being used by the ventilator as a source of power. The in-use indicators, as well as the other indicators, will be continuously lit when the battery pack assembly is in use. The indicators will be visible to a user without requiring the user to remove the battery pack assembly from the host. In another embodiment, when the battery pack assembly is not in use and is receiving power from the ventilator, the capacity indicators will continuously light to reflect the amount of charge remaining in the battery pack. The fault indicator will light if the battery has undergone a fault. The in-use indicator, however, will not be lit. As is the case when the battery pack assembly is in use, when the battery pack assembly is not in use and is receiving power from the ventilator, the indicators are visible to a user without requiring the user to remove the battery pack assembly from the host. In another embodiment, when the battery pack assembly is a stand alone battery pack assembly, the capacity indicators only light temporarily in response to a depressed test switch.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

The invention claimed is:

1. A battery pack assembly configured to power a ventilator, the battery pack assembly comprising:
   a connector communicatively coupled to a mating connector at the ventilator, the mating connector comprised of signal pins of different lengths;
   a battery pack comprising one or more battery cells;
   electronics for monitoring the status of the battery pack, the electronics sending a signal to stop charging when battery reaches a predetermined charge; and
   a battery pack assembly status indicator panel comprising one or more indicators on the exposed exterior of the battery pack assembly so that the indicators are visible to a user when the battery pack assembly is inserted into the ventilator, the indicators indicating battery status information.

2. The battery pack assembly of claim 1, the electronics further configured to provide power to the battery pack assembly status indicator when the battery pack is not receiving power from the ventilator.

3. The battery pack assembly of claim 1, wherein the status of the battery pack comprises information about at least one of: state of charge, battery current, voltage, assembly number, revision, number of discharges, number of charges, date, in-use status, and fault.

4. The battery pack assembly of claim 1, wherein the one or more indicators display the status of the battery pack about the battery's charge, in-use status, and fault.

5. The battery pack assembly of claim 4, wherein the information about fault includes information about over-charge, temperature, over-discharge, or voltage current charge.

6. The battery pack assembly of claim 1, wherein the one or more indicators are at least one of: a LED bar indicator and an alpha-numeric display.

7. The battery pack assembly of claim 1, wherein lighting the one or more indicators further comprises lighting the indicators displaying battery charge to correspond with the percentage of charge held by the battery, each indicator being lit when the battery reaches a certain percentage of charge.

8. The battery pack assembly of claim 1, wherein the battery pack assembly is hot swappable.

9. The battery pack assembly of claim 1, wherein the electronics is comprised of safety electronics and fuel gauge electronics.

10. The battery pack assembly of claim 1, wherein the electronics are controlled by integrated circuits.

11. The battery pack assembly of claim 1, wherein the predetermined charge is 100 Wt/hours.

12. A system for mechanical ventilation, the system comprising a battery pack assembly inserted into a ventilation system, the system further comprising:
   a pneumatic system for circulating breathing gases to and from a patient, the pneumatic system further comprising a compressor for pressurizing gases;
   a controller for controlling the operation of one or more inserted battery pack assemblies, wherein the controller is further configured:
      receive battery cell status information about the one or more inserted battery pack assemblies when the one or more inserted battery pack assemblies are not in use by the ventilator; and
      supply power used to light one or more indicators located on the exposed exterior of the one or more inserted battery pack assemblies so that a user can view the one or more indicators without removing the one or more inserted battery pack assemblies from the ventilator.

13. The system for mechanical ventilation of claim 12, the system further comprising at least one of the one or more battery pack assemblies inserted into a backplane of the compressor for use as an internal power supply.

14. The system for mechanical ventilation of claim 12, the system further comprising at least one of the one or more battery pack assemblies inserted into a side of the ventilation system for use as a back-up battery pack assembly.

15. The system for mechanical ventilation of claim 12, wherein the battery cell status information comprises information about at least one of state of charge, battery current, voltage, assembly number, revision, number of discharges, number of charges, date, in-use status, and fault.

16. The system for mechanical ventilation of claim 12, wherein the one or more indicators display the status of the battery cell about the battery's charge, in-use status, and fault.

17. The system for mechanical ventilation of claim 16, wherein the information about fault includes information about at least one of: over-charge, temperature, over-discharge.

18. The system for mechanical ventilation of claim 12, wherein the one or more indicators are at least one of: a LED bar indicator and an alpha-numeric display.

19. The system for mechanical ventilation of claim 12, wherein supply power to light the one or more indicators further comprises lighting the indicators displaying battery charge to correspond with the percentage of charge held by the battery, each indicator being lit when the battery reaches a certain percentage of charge.

20. The system for mechanical ventilation of claim 12, wherein the battery pack assembly is hot swappable.

* * * * *